(12) United States Patent
Polymeropoulos

(10) Patent No.: US 11,433,057 B2
(45) Date of Patent: Sep. 6, 2022

(54) METHOD FOR IMPROVING OR ENHANCING COGNITION

(71) Applicant: VANDA PHARMACEUTICALS INC., Washington, DC (US)

(72) Inventor: Mihael H. Polymeropoulos, Potomac, MD (US)

(73) Assignee: Vanda Pharmaceuticals Inc., Washington, DC (US)

( * ) Notice: Subject to any disclaimer, the term of this patent is extended or adjusted under 35 U.S.C. 154(b) by 296 days.

(21) Appl. No.: 16/097,750

(22) PCT Filed: May 19, 2017

(86) PCT No.: PCT/US2017/033468
§ 371 (c)(1),
(2) Date: Oct. 30, 2018

(87) PCT Pub. No.: WO2017/201364
PCT Pub. Date: Nov. 23, 2017

(65) Prior Publication Data
US 2020/0397765 A1  Dec. 24, 2020

Related U.S. Application Data

(60) Provisional application No. 62/339,527, filed on May 20, 2016.

(51) Int. Cl.
*A61K 31/439* (2006.01)
*A61P 25/28* (2006.01)

(52) U.S. Cl.
CPC ............ *A61K 31/439* (2013.01); *A61P 25/28* (2018.01)

(58) Field of Classification Search
CPC .............................. A61K 31/439; A61P 25/28
See application file for complete search history.

(56) References Cited

U.S. PATENT DOCUMENTS

2015/0275303 A1   10/2015   Feuerbach et al.

FOREIGN PATENT DOCUMENTS

| WO | 2011054759 A1 | | 5/2011 |
| WO | WO 2013010916 | * | 1/2013 |
| WO | WO 2013/057687 | * | 4/2013 |
| WO | WO 2014/091388 | * | 6/2014 |

OTHER PUBLICATIONS

"Metabolite—Encyclopedia.com", http://www.encyclopedia.com/doc/1E1-metabolit.html, accessed Jan. 25, 2008, publication date 2007 (Year: 2007).*
BEINAT. CNS Drugs, 2015, 29, 529-542 (Year: 2015).*
Notification of Transmittal of The International Search Report and Written Opinion of the International Searching Authority for PCT/US2017/033468 filed May 19, 2017; pp. 12.
Feuerbach, Dominik et al.; "AQW051, a novel, potent and selective alpha 7 nicotinic ACh receptor partial agonist: pharmacological characterization and phase 1 evaluation"; British Journal of Pharmacology; 2015; vol. 172; pp. 1292-1304; Abstract; pp. 1293; second column; first paragraph; p. 1302; third paragraph.

* cited by examiner

*Primary Examiner* — Noble E Jarrell
(74) *Attorney, Agent, or Firm* — Hoffman Warnick LLC

(57) ABSTRACT

Disclosed herein are a method for improving cognition in an individual having findings consistent with a cognitive impairment, and a method of enhancing cognition in an individual. The methods include administering a therapeutically effective amount of (R)-3-(6-p-tolyl-pyridin-3-yloxy)-1-aza-bicyclo[2.2.2]octane or a metabolite or a pharmaceutically acceptable salt thereof to the individual.

12 Claims, No Drawings

METHOD FOR IMPROVING OR ENHANCING COGNITION

CROSS REFERENCE TO RELATED APPLICATIONS

This application claims the benefit of U.S. Provisional Application No. 62/339,527, filed May 20, 2016, which is incorporated herein as though fully set forth herein.

BACKGROUND OF THE INVENTION

The application relates generally to pharmaceutical effects of alpha-7 nicotinic acetylcholine receptor (nAChR) agonists. More particularly, the application relates to the effects of alpha 7 nAChR agonists on cognition, including cognition enhancement and amelioration of cognitive impairments.

An "alpha-7 nAChR agonist" is a compound that binds in vivo and in vitro to a nAChR comprising an alpha-7 nAChR subunit and activates the receptor. Activation can be measured, e.g., by the method disclosed in WO2001/85727, i.e. a functional affinity assay at the homomeric alpha-7 nAChR carried out with a rat pituitary cell line stably expressing the alpha-7 nAChR. As read out, the calcium influx upon stimulation of the receptor compared to epibatidine is used. Alpha-7 nAChR agonists of the invention typically induce calcium influx of at least 50% of the maximal influx evoked by epibatidine with an $EC_{50}$ value of at least 1 µM.

In certain uses, an alpha-7 nAChR agonist that is selective for a receptor comprising a nAChR alpha 7 subunit may be desirable, since such an agonist would be expected to cause fewer side effects than a non-selective agonist to a treated subject. An agonist that is selective for a receptor comprising a nAChR alpha 7 subunit has a functional affinity to such a receptor to a much higher degree, e.g. at least 10-fold affinity difference in $EC_{50}$ value, preferably at least 20-fold, more preferably at least 50-fold, compared to any other nicotinic acetylcholine receptor.

To assess the affinity of the alpha-7 nAChR agonists of the invention on other nicotinic acetylcholine receptors, the method disclosed in WO2001/85727 can be used, i.e. to assess the affinity on human neuronal α4β2 nAChR, a similar functional assay is carried out using a human embryonic kidney cell line stable expressing the human α4β2 subtype. To assess the activity of the compounds of the invention on the "ganglionic subtype" and the "muscle type" of nicotinic acetylcholine receptor, similar functional assays are carried out with a human embryonic kidney cell line stably expressing the human "ganglionic subtype" or a cell line endogenously expressing the human "muscle type" of nicotinic acetylcholine receptors.

BRIEF DESCRIPTION OF THE INVENTION

A first aspect of the disclosure provides a method for improving cognition in an individual having findings consistent with a cognitive impairment, the method comprising: administering a therapeutically effective amount of the alpha 7 nAChR agonist, (R)-3-(6-p-tolyl-pyridin-3-yloxy)-1-azabicyclo[2.2.2]octane or a metabolite or a pharmaceutically acceptable salt thereof to the individual. In some embodiments, the individual may have a diagnosed cognitive impairment, which may be, e.g., Mild Cognitive Impairment (amnestic MCI), mild Alzheimer's Disease (AD), or another cognitive impairment, e.g., cognitive impairment as a clinically significant aspect of schizophrenia or other mental disease.

A second aspect of the disclosure provides a method of enhancing cognition in an individual, the method comprising: administering a therapeutically effective amount of the alpha 7 nAChR agonist, (R)-3-(6-p-tolyl-pyridin-3-yloxy)-1-aza-bicyclo[2.2.2]octane or a metabolite or a pharmaceutically acceptable salt thereof to the individual. Said individual may or may not be diagnosed with a cognitive impairment.

DETAILED DESCRIPTION OF THE INVENTION

It has been discovered that activators of the alpha 7 nicotinic acetylcholine receptor, particularly agonists thereof, and more particularly selective agonists thereof, may be used for the inventive methods described herein.

In one embodiment, the α7-nAChR agonist has a maximum molecular weight of 1500 dalton.

In one embodiment, the α7-nAChR agonist has a maximum molecular weight of 1000 dalton.

In one embodiment, the α7-nAChR agonist has a maximum molecular weight of 800 dalton.

In one embodiment, the α7-nAChR agonist has a maximum molecular weight of 500 dalton.

In one embodiment, the α7-nAChR agonist is a compound of formula (I)

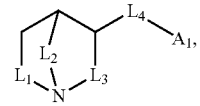

wherein
$L_1$ is —$CH_2$—; $L_2$ is —$CH_2$— or —$CH_2$—$CH_2$—; and $L_3$ is —$CH_2$— or —$CH(CH_3)$—; or
$L_1$ is —$CH_2$—$CH_2$—; $L_2$ is —$CH_2$—; and $L_3$ is —$CH_2$—$CH_2$—;
$L_4$ is a group selected from

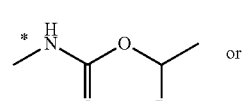

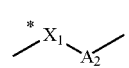

wherein the bond marked with the asterisk is attached to the azabicycloalkyl moiety;
$R_1$ is hydrogen or $C_{1-4}$alkyl;
$X_1$ is —O— or —NH—;
$A_2$ is selected from

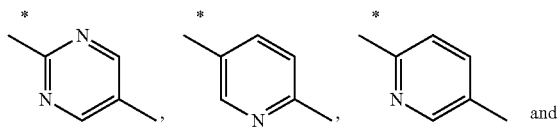

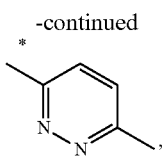

wherein the bond marked with the asterisk is attached to X₁;

A₁ is a five- to ten-membered monocyclic or fused polycyclic aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may be substituted once or more than once by R₂, and wherein a substituent on a nitrogen in a heterocyclic ring system may not be halogen;

each R₂ independently is $C_{1-6}$alkyl, $C_{1-6}$halogenalkyl, $C_{1-6}$alkoxy, $C_{1-6}$halogenalkoxy, halogen, cyano or a three- to six-membered monocyclic ring system which may be aromatic, saturated or partially saturated and which may contain from 1 to 4 hetero atoms selected from nitrogen, oxygen and sulfur, and wherein each ring system may contain not more than 2 oxygen atoms and not more than 2 sulfur atoms, and wherein each ring system may in turn be substituted once or more than once by $C_{1-6}$alkyl, $C_{1-6}$halogenalkyl, $C_{1-6}$alkoxy, $C_{1-6}$halogenalkoxy, halogen or cyano, and wherein a substituent on a nitrogen in a heterocyclic ring system may not be halogen;

or two R₂ at adjacent ring atoms form a $C_{3-4}$alkylene group, wherein 1-2 carbon atoms may be replaced by X₂, and wherein the $C_{3-4}$alkylene group may be substituted once or more than once by R₃;

each X₂ independently is —O— or —N(R₄)—;
each R₄ independently is hydrogen or $C_{1-6}$alkyl; and
each R₃ independently is halogen or $C_{1-6}$alkyl;
in free base form or in acid addition salt form.

Unless indicated otherwise, the expressions used in this invention have the following meaning:

"Alkyl" represents a straight-chain or branched-chain alkyl group, for example, methyl, ethyl, n- or iso-propyl, n-, iso-, sec- or tert-butyl, n-pentyl, n-hexyl; $C_{1-6}$alkyl preferably represents a straight-chain or branched-chain $C_{1-4}$alkyl with particular preference given to methyl, ethyl, n-propyl, iso-propyl and tert-butyl.

Each alkyl part of "alkoxy", "halogenalkyl" and so on shall have the same meaning as described in the above-mentioned definition of "alkyl", especially regarding linearity and preferential size.

A substituent being substituted "once or more than once", for example as defined for A₁, is preferably substituted by one to three substituents.

Halogen is generally fluorine, chlorine, bromine or iodine; preferably fluorine, chlorine or bromine. Halogenalkyl groups preferably have a chain length of 1 to 4 carbon atoms and are, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,2-trichloroethyl, 1,1,2,2-tetrafluoroethyl, 2,2,3,3-tetrafluoropropyl, 2,2,3,3,3-pentafluoropropyl or 2,2,3,4,4,4-hexafluorobutyl; preferably —CF3, —CHF2, —CH2F, —CHF—CH3, —CF2CH3, or —CH2CF3.

In the context of the invention, the definitions of "two R2 at adjacent ring atoms form a C3-4alkylene group, wherein 1-2 carbon atoms may be replaced by X2" or "two R5 at adjacent ring atoms form a C3-4alkylene group, wherein 1-2 carbon atoms may be replaced by X3" encompass —CH₂—CH₂—CH₂—, —CH₂—CH₂—CH₂—CH₂—, —O—CH₂—O—, —O—CH₂—CH₂—O— and —CH₂—CH₂—NH—. An example of a substituted group is —CH₂—CH₂—N(CH₃)—.

In the context of the invention, the definition of A₁ or A₃ as a "five- to ten-membered monocyclic or fused polycyclic aromatic ring system" encompasses a C₆- or C₁₀-aromatic hydrocarbon group or a five- to ten-membered heterocyclic aromatic ring system. "Polycyclic" means preferably bicyclic.

In the context of the invention, the definition of R₂ as a "three- to six-membered monocyclic ring system" encompasses a C₆-aromatic hydrocarbon group, a five- to six-membered heterocyclic aromatic ring system and a three- to six-membered monocyclic aliphatic or heterocyclic ring system.

A C₆- or C₁₀-aromatic hydrocarbon group is typically phenyl or naphthyl, especially phenyl.

Preferably, but also depending on substituent definition, "five- to ten-membered heterocyclic aromatic ring systems" consist of 5 to 10 ring atoms of which 1-3 ring atoms are hetero atoms. Such heterocyclic aromatic ring systems may be present as a single ring system or as bicyclic or tricyclic ring systems; preferably as single ring systems or as benz-annelated ring systems. Bicyclic or tricyclic ring systems may be formed by annelation of two or more rings, or by a bridging atom, e.g. oxygen, sulfur, nitrogen. Examples of heterocyclic ring systems are: imidazo[2,1-b]thiazole, pyrrole, pyrroline, pyrrolidine, pyrazole, pyrazoline, pyrazolidine, imidazole, imidazoline, imidazolidine, triazole, triazoline, triazolidine, tetrazole, furane, dihydrofurane, tetrahydrofurane, furazane (oxadiazole), dioxolane, thiophene, dihydrothiophene, tetrahydrothiophene, oxazole, oxazoline, oxazolidine, isoxazole, isoxazoline, isoxazolidine, thiazole, thiazoline, thiazolidine, isothiazole, isothiazoline, isothiazolidine, thiadiazole, thiadiazoline, thiadiazolidine, pyridine, piperidine, pyridazine, pyrazine, piperazine, triazine, pyrane, tetrahydropyrane, thiopyrane, tetrahydrothiopyrane, oxazine, thiazine, dioxine, morpholine, purine, pteridine, and the corresponding benz-annelated heterocycles, e.g. indole, isoindole, coumarin, isoquinoline, quinoline and the like. Preferred heterocycles are: imidazo[2,1-b]thiazole, oxazole, isoxazole, thiazole, isothiazole, triazole, pyrrole, furane, tetrahydrofurane, pyridine, pyrimidine, imidazole or pyrazole.

In the context of the invention, three- to six-membered monocyclic aliphatic ring systems are typically cyclopropyl, cyclobutyl, cyclopentyl or cyclohexyl.

On account of asymmetrical carbon atom(s) that may be present in the compounds of formula (I) and compounds of formula (II), the compounds may exist in optically active form or in form of mixtures of optical isomers, e.g. in form of racemic mixtures or diastereomeric mixtures. All optical isomers and their mixtures, including racemic mixtures, are part of the present invention.

Compounds of formula I are known to be selective agonists of the alapha-7 nAChR (see, e.g., WO12004022556). In particular, one compound of formula (I) that is known to be a selective agonist of the alpha-7 nAChR is (R)-3-(6-p-tolyl-pyridin-3-yloxy)-1-aza-bicyclo[2.2.2]octane, which has the following structure:

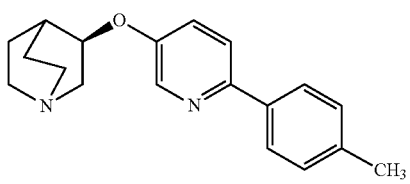

(R)-3-(6-p-tolyl-pyridin-3-yloxy)-1-aza-bicyclo[2.2.2]octane is also referred to as:
(R)-3-((6-(p-Tolyl)pyridin-3-yl)oxy)quinuclidine,
(3R)-3-{[6-(4-methylphenyl)pyridine-3-yl]oxy}-1-azabicyclo[2.2.2]octane,
and as AQW051.

Additional subject matter of the disclosure relates to a composition as described herein, and used for the inventive methods, wherein the alpha 7 nicotinic acetylcholine receptor activator is used as free base or pharmaceutically acceptable acid addition salt form. In another embodiment, the alpha 7 nicotinic acetylcholine receptor activator is in its free base or pharmaceutically acceptable acid addition salt form, in association with a pharmaceutical carrier or a diluent.

"Pharmaceutically acceptable salts" are known in the field (e.g. S. M. Berge, et al, "Pharmaceutical Salts", J. Pharm. Sd., 1977, 66:1-19; and "Handbook of Pharmaceutical Salts, Properties, Selection, and Use", Stahl, R H., Wermuth, C. G., Eds.; Wiley-VCH and VHCA: Zurich, 2002). A pharmaceutically acceptable salt is intended to mean a salt of a free form that is not toxic, biologically intolerable, or otherwise biologically undesirable. Preferred pharmaceutically acceptable salts are those that are pharmacologically effective and suitable for contact with the tissues of patients without undue toxicity, irritation, or allergic response.

In yet another embodiment, in the disclosed methods of treatment a second cognition enhancer or a therapeutic compound useful for the treatment of cognitive impairments, psychotic and/or neurodegenerative disorders, such as a conventional antipsychotic or an atypical antipsychotic, can be administered. Preferably, a combination being a pharmaceutical composition or a combined pharmaceutical preparation is used. Such a pharmaceutical composition can be administered together, one after the other or separately in one combined unit dosage.

In another aspect of the disclosed methods, the alpha 7 nicotinic acetylcholine receptor activator dose to be administered is from about 1 mg to about 100 mg per day. Alternatively, the dose to be administered is from about 2 mg to about 100 mg, or about 3 mg to about 90 mg, or about 4 mg to about 80 mg, or about 5 mg to about 70 mg, or about 6 mg to about 60 mg, or about 7 mg to about 50 mg, or about 8 mg to about 40 mg, or about 9 mg to about 35 mg, or about 10 mg to about 30 mg per day, or about 5 mg to about 10 mg, or about 10 mg to about 15 mg, or about 15 mg to about 20 mg, or about 20 mg to about 25 mg per day. In one embodiment of said aspects, the alpha 7 nicotinic acetylcholine receptor activator is an alpha 7 nicotinic acetylcholine receptor agonist.

Actual dosage levels of the active agents in the pharmaceutical compositions of the present invention may be varied so as to obtain an amount of the active agent which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

Administration of a "therapeutically effective dosage" or a "therapeutically effective amount" of an alpha 7 nicotinic acetylcholine receptor activator comprised in the compositions of the invention can result in a decrease in severity of disease symptoms, an increase in frequency and duration of disease symptom-free periods, or a prevention of impairment or disability due to the disease affliction i.e. an improvement of cognitive skills.

A composition of the present invention can be administered by one or more routes of administration using one or more of a variety of methods known in the art. As will be appreciated by the skilled artisan, the route and/or mode of administration will vary depending upon the desired results. Routes of administration may include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrastemal injection and infusion. Alternatively, a composition can be administered by a non-parenteral route, such as a topical, epidermal or mucosal route of administration, for example, intranasally, orally, vaginally, rectally, sublingually or topically.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g. Sustained and Controlled Release Drug Delivery Systems, J. R. Robinson, ed., Marcel Dekker, Inc., New York, 1978. Preferred therapeutic compositions are compositions for oral or transdermal administration. A composition for enteral or parenteral administration is, for example, a unit dosage form, such as a sugar-coated tablet, a tablet, a capsule, a suppository or an ampoule.

The unit content of active ingredients in an individual dose need not in itself constitute a therapeutically effective amount, since such an amount can be reached by the administration of a plurality of dosage units. A composition according to the invention may contain, e.g., from about 10% to about 100%, preferably from about 20% to about 60%, of the active ingredients.

If not indicated otherwise, a pharmaceutical composition according to the invention is prepared in a manner known per se, e.g. by means of conventional mixing, granulating, sugar-coating, dissolving or lyophilizing processes. In preparing a composition for an oral dosage form, any of the usual pharmaceutical media may be employed, for example water, glycols, oils, alcohols, carriers, such as starches, sugars, or microcrystalline cellulose, diluents, granulating agents, lubricants, binders, disintegrating agents and the like. Because of their ease of administration, tablets and capsules represent the most advantageous oral dosage unit forms, in which case solid pharmaceutical carriers are obviously employed.

General Definitions

In order that the present invention may be more readily understood, certain terms are first defined. Additional definitions are set forth throughout the detailed description.

The term "comprising" means "including" e.g. a composition "comprising" X may consist exclusively of X or may include something additional e.g. X+Y.

The term "about" in relation to a numerical value x means, for example, x±10%.

The term "cognition enhancer" in the context of this disclosure refers to any drug, supplement, nutraceutical, or functional food that is said to improve mental functions such as cognition, memory, intelligence, motivation, attention, and concentration.

Cognition enhancers, as used herein include, but are not limited to cholinergic compounds like acetylcholine esterase inhibitors and/or buturylesterase inhibitors (rivastigmine, donezepil, galantamine, huperzine), ampakines (e.g. CX614, CX516), muscarinic modulators (e.g. muscarinic receptor agonists), modulators of the NMDA-receptor (e.g. positive modulators, antagonists, memantine), phosphodiesterase inhibitors (e.g. PDE4 inhibitors), nootropic compounds like hydergine, oxiracetam, aniracetam, acetyl-L-camitine, ginko-derived compounds, compounds contained in gerovitals like p-aminobenzoic acid and dithylaminoethanol and derivative thereof and attention-modulating compounds like methylphenicate, tomoxetine and modafinil.

The term "conventional antipsychotics" denotes compounds that are effective in treating psychoses mainly via dopamine receptor D2 antagonism. "Conventional antipsychotics" as used herein includes, but is not limited to haloperidol, droperidol, molindone, fluphenazine, thiotixene, flupentixol, promazine, pimozide, chlorpromazine, methotrimeprazine, pipotiazine trifluoperazine, thioridazine, acetophenazine, chlorprothixene and mesoridazine.

The term "atypical antipsychotics" denotes compounds that are effective in treating psychoses via an additional and/or different mechanism than dopamine receptor 2 antagonism. "Atypical antipsychotics" as used herein includes, but is not limited to iloperidone, clozapine, risperidone, olanzapine, quetiapine, ziprasidone, aripiprazol, sertindole, perphenazine, mesoridazine, prochlorperazine, naproxene and loxapine.

The term "mild cognitive impairment" (MCI) in the context of this disclosure refers to a cognitive impairment beyond that expected for an individual of a certain age and education, but that do not interfere significantly with the daily activities of such an individual (Petersen R C, Smith G E, Waring S C, Ivnik R J, Tangalos E G, Kokmen E (1999). "Mild cognitive impairment: clinical characterization and outcome". Arch. Neurol. 56 (3): 303-8.) The term "subject" as used herein refers preferably to a human being, especially to a patient being diagnosed with a cognitive impairment, Alzheimer's Disease, schizophrenia or another mental disease which is a acquired deficit in one or more of memory function, problem solving, orientation and/or abstraction that impinges on an individual's ability to function independently. Subject, patient or individual are used interchangeably.

The term "cognitive disorders/impairments" and "psychotic and/or neurodegenerative disorders" refer to a mental diseases which are acquired deficits in one or more of memory function, problem solving, orientation and/or abstraction that impinges on an individual's ability to function independently. Examples of said disorders are Alzheimer's disease, Lewy Body Dementia, Amyotrophic Lateral Sclerosis, memory impairment, memory loss, cognition deficit, attention deficit, hyperactivity Disorder, schizophrenia, Parkinson's disease, dementia and vascular dementia.

Preparation

The following section and examples disclose further aspects relating to this technology:

Example A: Preparation of 5-choro-2-(4-methypheny)pyridine

Under nitrogen 2,5-dichloro-pyridine (40 g, 270 mmol), 4-methylphenylboronic acid (39 g, 289 mmol) and bistriphenylphosphin-palladium(II) dichloride (1.14 g; 1.6 mmol) were suspended in water (258 g)/THF (117 g) for approx. 30 min at 35-55° C. A solution of tripotassium phosphate (143.4 g, 676 mmol) in water (143 g) was added at 35-55° C. during approx. 60-120 min and 55° C. was maintained for another approx. 30-45 min. More tripotassium phosphate (22.9 g, 108 mmol) in water (22.9 g) was added over a period of approx. 30 min and the temperature was raised to 55-60° C. to complete the reaction within another approx. 2 h.

For extractive palladium removal a solution of cysteine (ca. 16 g) in water (115 g) was added to the reaction mixture at 60-55° C. After approx. 1 h at 55° C. the biphasic reaction mixture was clarified by filtration over a pad of cellflock filter aid (2-5 g) and a THF/water mixture (110 g/75 g) was used for rinsing. The layers of the combined filtrates were separated at 25° C. and the salt containing water layer was extracted with THF (1×57 g). The combined THF layers were diluted with ethanol 94% (195 g) and concentrated by distillation under reduced pressure (300-200 mbar) at a jacket temperature of 45° C. in order to remove the bulk of THF (175-250 g). To the remaining product solution further ethanol (97 g) was added and at 45-55° C. water (565 g) was gradually added over a period of approx. 60 min to induce and maintain crystallization. After 30 min the temperature was lowered to approx. 20° C. in approx. 90-120 min and after another hour at that temperature the solids were collected by filtration, washed with ethanol/water 1:2 and dried under reduced pressure to yield 5-chloro-2-(4-methylphenyl)pyridine (52.5 g; 95% of theory; purity>95%; Pd<25 ppm).

Example B: Preparation of (R)-3-(6-(4-methyphenyl)-pyridin-3-yloxy)-1-aza-bicyclo[2.2.2]octane in Free Form and Fumarate Salt Form Example B1: Formation of Free Form Under nitrogen, to 3R-quinuclidinol (43.8 g, 0.34 mol) in DMSO (792 g) an approx. 20% THF solution of potassium tert-butoxide (210 g, 0.375 mol) was added and at approx. 40-45° C. under reduced pressure the THF solvent was distilled off. The temperature of the reaction mixture was raised to 90° C. and the solid 5-chloro-2-(4-methylphenyl)pyridine (61.2 g, 0.30 mol) was gradually added in at least 4 portions. The temperature was raised further to approx. 100-105° C. and after at least another 3 hours at this temperature the reaction to (R)-3-(6-(4-methylphenyl)-pyridin-3-yloxy)-1-aza-bicyclo[2.2.2]octane was complete.

Water (150 g) was added to the reaction mixture at 60-25° C. and the temperature was gradually lowered to approx. 20° C. in approx. 60 min and additional water (210 g) was added. After at least another 2 further hours at this temperature the fine solids were collected by filtration, washed successively with DMSO/water (approx. 322 g; 2:1 mixture), water (500 g) and water/ethanol (approx. 500 g; 9:1 mixture) and dried at 60° C. under reduced pressure to yield (R)-3-(6-(4-methylphenyl)-pyridin-3-yloxy)-1-aza-bicyclo[2.2.2]octane (56.3 g, 63% of theory).

Example B2: Formation of Fumarate Salt Form

To a clear solution of (R)-3-(6-(4-methylphenyl)-pyridin-3-yloxy)-1-aza-bicyclo [2.2.2] octane (39.6 g; 0.135 mol) and fumaric acid (16.4 g, 0.141 mol) in ethanol (330 g)/water (21 g) at 65° C. tert.-butylmethylether (142.5 g) was added and the reaction mixture was cooled to 23° C. in approx. 60 min. Further tert.-butylmethylether (170.6 g) was added. After at least another 2 hours the solids were collected by filtration, washed with ethanol/tert.butymethylether (153 g; 1.1 mixture) and dried at 55-60° C. under reduced pressure to yield (R)-3-(6-(4-methylphenyl)-pyridin-3-yloxy)-1-aza-bicyclo[2.2.2]octane hydrogenfumarate (43.8 g, 79% of theory).

Example C: Preparation of (R)-3-(6-(4-methylphenyl)-pyridin-3-yloxy)-1-aza-bicyclo[2.2.2]octane in Free Form and Fumarate Salt Form Example C$_1$: Formation of Free Form Under nitrogen to 3R-quinuclidinol (41.4 g, 0.325 mol) in DMSO (320 g) a solution of 5-chloro-2-(4-methylphenyl) pyridine (51 g, 0.250 mol) in toluene (201 g) was added. The temperature was raised gradually to approx. 100-105° C. while residual water, if any, was removed by refluxing under reduced pressure at a water trap for ca. 45 min. Over a period of approx. 90 min an approx. 20% THF solution of potassium tert-butoxide (158.8 g, 0.283 mol) was continuously added while gradually the THF solvent distills off. After another 2-5 hours at approx. 100-105° C. the reaction to (R)-3-(6-(4-methylphenyl)-pyridin-3-yloxy)-1-aza-bicyclo [2.2.2]octane was complete.

Water (293 g) was added to the reaction mixture at 60-25° C. The layers were separated and the toluene layer was washed with water (2×42 g). The toluene solution was dried at ca. 60° C. by refluxing under reduced pressure at a water trap for ca. 45-60 min.

Example C2: Formation of Fumarate Salt Form

To the toluene solution of Example C1, at ca. 50-55° C., a slurry of fumaric acid (26.1 g, 0.9 eq) in EtOH 94% (22 g) and toluene (97 g) was gradually added. Further toluene (97 g) was added for rinsing and after another ca. 30-60 min at 55° C. the temperature was gradually lowered to approx. 20° C. in approx. 120-180 min. After at least another 1 hour the solids were collected by filtration, washed with water saturated toluene (2×104 g) and dried at 60° C. under reduced pressure to yield (R)-3-(6-(4-methylphenyl)-pyridin-3-yloxy)-1-aza-bicyclo[2.2.2]octane hydrogenfumarate (84.8 g; 82% of theory, based on amount of 5-chloro-2-(4-methylphenyl)pyridine used in Example C1).

Example D: Preparation of Mono-Fumarate Salt of (R)-3-(6-(methylphenyl)-pyridin-3-yloxy)-1-aza-bicyclo[2.2.2]octane in Crystalline Form 500 mg of (R)-3-(6-(4-methylphenyl)-pyridin-3-yloxy)-1-aza-bicyclo[2.2.2]octane in free base form were suspended in 20 ml isopropyl alcohol. A stochiometric amount of fumaric acid was added. The resulting solution was stirred at ambient temperature for 14 hours. The precipitate was collected by filtration.

Example D1: Preparation of Mono-Fumarate Salt of (R)-3-(6-(methylphenyl)-pyridin-3-yloxy)-1-aza-bicyclo[2.2.2]octane in Crystalline Form by Seeded Crystallization 7.3 g mono-fumarate of (R)-3-(6-(4-methylphenyl)-pyridin-3-yloxy)-1-aza-bicyclo [2.2.2]octane (purity >98%; prepared as described e.g. in Example C2) was dissolved in ethanol (42.9 g)/isopropanol (8.5 g)/water (7.2 g) at about 50° C., clarified by filtration and added at this temperature gradually over a period of about 8 hours to filtered tertiary-butylmethylether (118.4 g) at temperature of about 50. After about 25% of the filtrate was added, an ultrasonificated suspension of seed crystals of the mono-fumarate of (R)-3-(6-(4-methylphenyl)-pyridin-3-yloxy)-1-aza-bicyclo[2.2.2] octane (6 mg, prepared e.g. as described in Example C2) in isopropanol (0.1 ml) was added to induce crystallization. The product suspension was maintained for another 1 hour at 50° C. and cooled to 0° C. within 8 hours. After another 1 hour at this temperature the solids were isolated by filtration, washed with isopropanol/tertiary-butylmethylether (402 1:1 mixture and dried at about 50° C. under reduced pressure to yield the mono-fumarate of (R)-3-(6-(4-methylphenyl)-pyridin-3-yloxy)-1-aza-bicyclo[2.2.2]octane (5.85 g; 81% of theory; purity >99.5%).

Example E: Hard Capsules

Hard gelatin capsules, each comprising as active ingredient 0.5, 5 or 25 mg of the mono-fumarate of (R)-3-(6-(4-methylphenyl)-pyridin-3-yloxy)-1-aza-bicyclo[2.2.2]octane can be prepared as follows:

| Ingredient for capsule fill | % (w/w) for 0.5 mg capsules | % (w/w) for 5 mg capsules | % (w/w) for 25 mg capsules |
| --- | --- | --- | --- |
| Mono-fumarate of (R)-3-(6-(4-methylphenyl)-pyridin-3-yloxy)-1-aza-bicyclo[2.2.2]octane | 0.46 | 4.65 | 23.23 |
| Lactose monohydrate | 65.24 | 61.05 | 42.47 |
| Microcrystalline cellulose | 25.00 | 25.00 | 25.00 |
| Hypromellose | 2.50 | 2.50 | 2.50 |
| Sodium croscarmellose | 6.00 | 6.00 | 6.00 |
| Colloidal silicon dioxide | 0.30 | 0.30 | 0.30 |
| Magnesium stearate | 0.50 | 0.50 | 0.50 |
| Purified water* | q.s. | q.s. | q.s. |

*removed during processing

Preparation process: Mono-fumarate of (R)-3-(6-(4-methylphenyl)-pyridin-3-yloxy)-1-aza-bicyclo[2.2.2]octane, lactose monohydrate, microcrystalline cellulose, a portion of sodium croscarmellose and hypromellose were dry mixed in a high shear mixer bowl, and granulating fluid (purified water) added. Once the granulation was complete, the wet granules were dried in a fluid bed drier and the dry granules were milled. The remaining sodium croscarmellose and colloidal silicon dioxide were passed through a suitable sieve and added to the dried granular material and blended in a suitable blending shell. This was achieved by co-sieving the sodium croscarmellose and the colloidal silicon dioxide with a portion of the milled granules through a suitable sieve into the blending shell. Similarly, the required amount of sieved magnesium stearate was added to the bulk granule and then mixed in the same blending shell. This final blend was encapsulated into capsules using automated equipment. Weight ratio of capsule fill to empty capsule shells was 2:1.

Example F: Tablets

Example F1: Film-Coated Tablet

Film-coated tablets containing e.g. 0.5 mg of the mono-fumarate of (R)-3-(6-(4-methylphenyl)-pyridin-3-yloxy)-1-aza-bicyclo[2.2.2]octane may be prepared as follows:
Preparation of Ore-Mix:
Weigh-in mono-fumarate of (R)-3-(6-(4-methylphenyl)-pyridin-3-yloxy)-1-aza-bicyclo[2.2.2]octane (e.g. approx. 0.7%) and maize starch (e.g. approx. 13%), mix in a tumble blender (approx 100-300 rotations), pass through a sieve of approx. 0.25-1.0 mm mesh-size. Mix in a tumble blender (approx. 100-300 rotations).
Preparation of Final Blend:
To above pre-mix add microcrystalline cellulose (e.g. approx. 25%), sprayed lactose (e.g. approx. 68%), sodium-carboxymethylcellulose XL (e.g. approx. 2%) and Aerosil (e.g. approx. 0.5%) and mix in a tumble blender (approx. 100-300 rotations). Pass this mixture through a sieve of approx. 0.5-1.0 mm mesh-size and mix again (approx. 100-300 rotations). Add the sodium-stearyl-fumarate (e.g. approx. 1.5%) through a handsieve at approx. 0.5-1.0 mm mesh-size and mix in a tumble blender (approx. 30-150 rotations).
Compression:
On a rotary press compress the above final blend to cores of approx. 100 mg, using the dosage specific tooling (e.g. approx. 6 mm, round, curved).
Coating:
Prepare a suspension in water with basic coating premixes black, red, yellow and/or white. Coat the above obtained cores in a perforated coating pan, and dry.

Example F2: Bilayer Film-Coated Tablet

Bilayer film-coated tablets containing e.g. 2.5 mg of the mono-fumarate of (R)-3-(6-(4-methylphenyl)-pyridin-3-yloxy)-1-aza-bicyclo[2.2.2]octane may be prepared as follows:
Final Active Blend:
Weigh-in mono-fumarate of (R)-3-(6-(4-methylphenyl)-pyridin-3-yloxy)-1-aza-bicyclo[2.2.2]octane coarse (e.g. approx. 15.5%), microcrystalline cellulose (e.g. approx. 25%), sprayed lactose (e.g. approx. 53%), sodium-carboxymethylcellulose XL (e.g. approx. 3%) and Aerosil (e.g. approx. 0.5%) and mix in a tumble blender (approx 100-300 rotations). Pass this mixture through a sieve of approx. 0.5-1.0 mm mesh-size and mix again (approx 100-300 rotations).
Add the Na-stearyl-fumarate (e.g. approx. 3%) through a handsieve at approx. 0.5-10 mm and mix in a tumble blender (approx 30-150 rotations).
Final Placebo Blend:
Weigh-in microcrystalline cellulose (e.g. approx. 26%), sprayed lactose (e.g. approx. 69%), sodium-carboxymethylcellulose XL (e.g. approx. 1.9%) and Aerosil (e.g. approx. 0.5%) and mix in a tumble blender (approx 100-300 rotations). Pass this mixture through a sieve of approx. 0.5-1.0 mm mesh-size and mix again (approx 100-300 rotations).
Add the sodium-stearyl-fumarate (e.g. approx. 3%) through a handsieve at approx. 0.5-1.0 mm and mix in a tumble blender (approx 30-150 rotations).
Compression:
On a rotary press compress the above final blends to a bilayer tablet-core of approx. 100 mg with one placebo layer (approx. 77.5 mg) and one active layer (approx. 22.5 mg), using the dosage specific tooling (e.g. approx. 6 mm, round, curved).
Coating:
Prepare a suspension in water with basic coating premixes black, red, yellow and/or white. Coat the above obtained cores in a perforated coating pan, and dry.

Example F3: Film-Coated Tablet

Film-coated tablets containing e.g. 50 mg of the mono-fumarate of (R)-3-(6-(4-methylphenyl)-pyridin-3-yloxy)-1-aza-bicyclo[2.2.2]octane may be prepared as follows:
Final Blend:
Weigh-in mono-fumarate of (R)-3-(6-(4-methylphenyl)-pyridin-3-yloxy)-1-aza-bicyclo[2.2.2]octane coarse (e.g. approx. 15.5%), microcrystalline cellulose (e.g. approx. 25%), sprayed lactose (e.g. approx. 53%), sodium-carboxymethylcellulose XL (e.g. approx. 3%) and Aerosil (e.g. approx. 0.5%) and mix in a tumble blender (approx. 100-300 rotations). Pass this mixture through a sieve of approx. 0.5-1.0 mm mesh-size and mix again (approx. 100-300 rotations).
Add the sodium-stearyl-fumarate (e.g. approx. 3%) through a handsieve at approx. 0.5-10 mm and mix in a tumble blender (approx. 30-150 rotations).
Compression:
Compress the above final blend on a rotary press to cores, using the dosage specific tooling (e.g. approx. 15*5.9 mm, round, curved).
Coating:
Prepare a suspension in water with basic coating premixes black, red, yellow and/or white. Coat the above obtained cores in a perforated coating pan, and dry.

Example 1

The following example illustrates the methods of the invention, in which a 4-week, parallel-group, randomized, double-blind, placebo-controlled, adaptive proof of concept study of AQW051 at up to three dose levels for the treatment of patients with findings consistent with mild Alzheimer's disease (AD) or Mild Cognitive Impairment (amnestic MCI) was conducted in two stages.
Objectives
Primary Objective(s):
To assess AQW051 as a cognitive enhancer, as measured by selected tests [Paired Associates Learning (PAL), Spatial Working Memory (SWM), Rapid Visual Information Processing (RVP)] from the Cambridge Neuropsychological Test Automated Battery (CANTAB) computerized cognitive test battery, in patients with findings consistent with mild AD or amnestic MCI.
Key Secondary Objective(s)
To explore effects of AQW051 on other cognitive functions not assessed by the primary measures (CANTAB tests Pattern Recognition Memory (PRM), Choice Reaction Time (CRT), Graded Naming Test-Revised (GNT).

To explore the safety and tolerability of AQW051 in patients with findings consistent with mild AD or amnestic MCI.

Test Product(s), Dose(s), and Mode(s) of Administration

The investigational drug AQW51 was provided as either 0.5 mg, 5 mg, or 25 mg capsules. In stage I only 5 mg capsules were used. All groups received 15 mg of AQW051 daily for 4 weeks.

On Day 1, 8, 15, 22 and 28, the study drug was administered by study personnel and was taken orally with 240 ml of water after light breakfast. On all other study treatment days, patients self-administered the study medication in the morning after light breakfast.

Statistical Methods

The different CANTAB readouts were analyzed separately by rank analyses of covariance, including "treatment" and "stratum" (MCI, AD) as fixed effects and the corresponding baseline value as covariate. The comparison of interest was the contrast between active treatment and placebo; tests were performed to the one-sided 10% level without multiplicity-adjustment. Point and interval estimates were produced by the baseline-adjusted stratified Hodges-Lehmann method. In addition, sensitivity analyses were performed using standard analyses of covariance, to complement the aforementioned nonparametric methods. The items "errors at the 6 pattern stage" and "total trials adjusted" of the PAL task at day 28 played a key role at the interim analysis. At the end of stage 1, the conditional power of the study to reach an overall significant result in both these key endpoints at the final analysis was estimated by bootstrap methods. The different scores from the ADAS-Cog, QoL-AD, the DAD and the MMSE were analyzed using standard analyses of covariance. Safety and tolerability variables measures were analyzed by means of descriptive statistics.

Study Population

Inclusion Criteria:
  Willing and able to give written informed consent
  Meet the diagnostic criteria for either amnestic MCI or mild AD.
  Structural brain scan within the last 6 months prior to randomization that indicates no other underlying disease, in particular no evidence for vascular pathology except for normal age-related white matter/incidental white matter changes which is normal for this age group.
  Daily contact with a primary caregiver/partner Exclusion Criteria:
  Immune therapy targeting Alzheimer beta amyloid within the last 12 months
  Institutionalized
  Disability that may prevent completion of all study requirements (e.g., blindness, deafness, or communication difficulty)
  Reported use of tobacco products in the previous 3 months or have a urine cotinine level greater than 500 ng/ml
  Past medical history of clinically significant electrocardiogram (ECG) abnormalities or a family history (grandparents, parents, and siblings) of prolonged QT-interval syndrome
  History or current diagnosis of conditions specified in the protocol.
  Other protocol-defined inclusion/exclusion criteria may apply.

Participant Flow Table

Patient Disposition—n (%) of Patients

| Disposition Reason | All Treatments N = 54 | AQW051 15 mg N = 27 | Placebo N = 27 |
|---|---|---|---|
| Completed | 54 (100%) | 27 (100%) | 27 (100%) |

Baseline Characteristics

| | | AQW051 15 mg N = 27 | Placebo N = 27 | All Treatments N = 54 |
|---|---|---|---|---|
| Age (years) | Mean (SD) | 69.4 (6.05) | 71.9 (7.14) | 70.6 (6.68) |
| | Median | 67.0 | 74.0 | 70.0 |
| | Range | 60-83 | 56-84 | 56-84 |
| Gender n (%) | Male | 14 (52%) | 10 (37%) | 24 (44%) |
| | Female | 13 (48%) | 17 (63%) | 30 (56%) |
| Race n (%) | Caucasian | 27 (100%) | 27 (100%) | 54 (100%) |
| Ethnicity n (%) | Other | 27 (100%) | 27 (100%) | 54 (100%) |
| Disease group - n (%) | Alzheimer's disease | 7 (26%) | 9 (33%) | 16 (30%) |
| | Mild Cognitive Impairment | 20 (74%) | 18 (67%) | 38 (70%) |
| Body Mass Index (kg/m2) | Mean (SD) | 26.42 (4.023) | 25.25 (4.531) | 25.83 (4.285) |
| | Median | 26.17 | 23.53 | 25.10 |
| | Range | 18.2-36.2 | 19.5-35.4 | 18.2-36.4 |
| Weight (kg) | Mean (SD) | 73.76 (12.09) | 68.53 (13.073) | 71.15 (12.748) |
| | Median | 74.00 | 69.00 | 72.00 |
| | Range | 49.5-98.0 | 49.0-98.0 | 49.0-98.0 |
| Height (cm) | Mean (SD) | 167.0 (6.95) | 164.8 (10.42) | 165.9 (8.84) |
| | Median | 166.0 | 164.0 | 165.0 |
| | Range | 151-179 | 151-193 | 151-193 |

Summary of Efficacy
Primary Outcome Result(s)
Summary of Statistical Analyses of CANTAB Statistically Significant Endpoints for all Patients and MCI Patients Only

| Population Target variable | Study day | N | Difference AQW051 15 mg vs. Placebo | LCL of Difference | UCL of Difference | p-value of test vs. placebo |
|---|---|---|---|---|---|---|
| All patients | | | | | | |
| PAL | | | | | | |
| PAL total errors (2 shapes adj) | 1 | 54 | 0 | −1 | 0 | 0.0142 |
| PAL total trials (adj) | 1 | 54 | −1 | −3 | 1 | 0.0846 |
| PAL total errors (6 shapes adj) | 1 | 54 | −2 | −5 | 2 | 0.0840 |
| SWM | | | | | | |
| Between errors (4 boxes) | 28 | 54 | −0.5 | −2 | 1 | 0.0866 |
| Between errors (6 boxes) | 28 | 54 | −2 | −4 | 1 | 0.0430 |
| Between errors | 28 | 54 | −3.5 | −10 | 2 | 0.0701 |
| RVP | | | | | | |
| Mean latency | 1 | 54 | −21.5 | −42 | 1 | 0.0292 |
| CRT | | | | | | |
| Percent correct trials | 28 | 54 | 0.5 | −1 | 1 | 0.0632 |
| MCI patient only | | | | | | |
| PAL | | | | | | |
| PAL of total errors (2 shapes adj) | 1 | 38 | 0 | −1 | 0 | 0.0239 |
| Total trials (adj) | 1 | 38 | −1.5 | −4 | 1 | 0.0877 |
| SWM | | | | | | |
| Between errors (6 boxes) | 28 | 38 | −2.5 | −5 | 1 | 0.0290 |
| Between errors | 28 | 38 | −5 | −12 | 3 | 0.0845 |
| RVP | | | | | | |
| Mean latency | 1 | 38 | −22 | −48 | 4 | 0.0419 |
| CRT | | | | | | |
| Percent correct trials | 28 | 38 | 0.5 | −1 | 1 | 0.0918 |
| Median latency | 28 | 38 | −23 | −59 | 19 | 0.0966 |

* One sided p-value, α < 0.1
LCL: lower 95% confidence limit;
UCL: upper 95% confidence limit Key Secondary Outcome Result(s)
Statistical analysis of CANTAB-GNT Statistical analysis of CANTAB - GNT
PD analysis set

| Target variable | Study day | N | Difference, AQW051 15 mg vs. placebo | LCL of Difference | UCL of Difference | p-value of test vs. placebo |
|---|---|---|---|---|---|---|
| Total correct | 28 | 54 | −1.5 | −5 | 3 | 0.8191 |

Difference to Placebo: stratified Hodges-Lehmann estimate and confidence limits

Test vs. Placebo: stratified rank analysis of covariance, one-sided p-value

Estimates and confidence limits are restricted to integer values. If two neighbouring integers are equally valid as point estimates, they are averaged.
LCL: lower 95% confidence limit;
UCL: upper 95% confidence limit Statistical analysis of CANTAB-PRM

| Target variable | Study day | N | Difference, AQW051 15 mg vs. placebo | LCL of Difference | UCL of Difference | p-value of test vs. placebo |
|---|---|---|---|---|---|---|
| | | | Statistical analysis of CANTAB - PRM PD analysis set | | | |
| Percent correct immediate | 28 | 54 | −4 | −10 | 8 | 0.8090 |
| Percent correct delayed | 28 | 54 | 0 | −9 | 9 | 0.4244 |
| Mean correct latency immediate | 28 | 54 | 198 | −212 | 693 | 0.8328 |
| Mean correct latency delayed | 28 | 54 | 150 | −168 | 515 | 0.7864 |

Difference to Placebo: stratified Hodges-Lehmann estimate and confidence limits
Test vs. Placebo: stratified rank analysis of covariance, one-sided p-value
Estimates and confidence limits are restricted to integer values. If two neighboring integers are equally valid as point estimates, they are averaged.
LCL: lower 95% confidence limit;
UCL: upper 95% confidence limit Statistical Analysis of CANTAB-CRT

| Target variable | Study day | N | Difference, AQW051 15 mg vs. placebo | LCL of Difference | UCL of Difference | p-value of test vs. placebo |
|---|---|---|---|---|---|---|
| | | | Statistical analysis of CANTAB - CRT PD analysis set | | | |
| Percent correct trials | 28 | 54 | 0.5 | −1 | 1 | 0.0632 |
| Median latency | 28 | 54 | −9.5 | −40 | 46 | 0.3273 |

Difference to Placebo: stratified Hodges-Lehmann estimate and confidence limits
Test vs. Placebo: stratified rank analysis of covariance, one-sided p-value
Estimates and confidence limits are restricted to integer values. If two neighbouring integers are equally valid as point estimates, they are averaged.
LCL: lower 95% confidence limit;
UCL: upper 95% confidence limit Summary of Safety
Safety Results
Adverse Events by System Organ Class: Adverse Events Overall and Frequently Affected System Organ Classes—n (%) of Subjects (all Patients in any Group) Safety Analysis Set

| Body system | AQW051 15 mg N = 27 n | (%) | Placebo N = 27 n | (%) | Total N = 54 n | (%) |
|---|---|---|---|---|---|---|
| Patients with AEs | 11 | (40.7) | 10 | (37.0) | 21 | (38.9) |
| Nervous system disorders | 2 | (7.4) | 4 | (14.8) | 6 | (11.1) |
| Infections and infestations | 3 | (11.1) | 2 | (7.4) | 5 | (9.3) |
| Gastrointestinal disorders | 2 | (7.4) | 2 | (7.4) | 4 | (7.4) |
| Musculoskeletal and connective tissue disorders | 2 | (7.4) | 2 | (7.4) | 4 | (7.4) |
| Injury, poisoning and procedural complications | | | 3 | (11.1) | 3 | (5.6) |
| Eye disorders | 1 | (3.7) | 1 | (3.7) | 2 | (3.7) |
| Respiratory, thoracic and mediastinal disorders | 1 | (3.7) | 1 | (3.7) | 2 | (3.7) |
| Skin and subcutaneous disorders | 2 | (7.4) | | | 2 | (3.7) |
| Ear and Labyrinth disorders | 1 | (3.7) | | | 1 | (1.9) |
| Hepatobiliary disorders | 1 | (3.7) | | | 1 | (1.9) |
| Psychiatric disorders | | | 1 | (3.7) | 1 | (1.9) |

Under one treatment, a subject with multiple occurrences of an adverse event is counted only once in the AE category. N=number of subject studied; n=number of subjects with at least 1 AE in the category. Only adverse events occurring at or after first drug intake are included.

Adverse Events Overall and Most Frequent Events—n (%) of Subjects (all Patients in any Group) Safety Analysis Set

| Body system | AQW051 15 mg N = 27 n | (%) | Placebo N = 27 n | (%) | Total N = 54 n | (%) |
|---|---|---|---|---|---|---|
| Patients with AE(s) | 11 | (40.7) | 10 | (37.0) | 21 | (38.9) |
| Headache | 2 | (7.4) | 4 | (14.8) | 6 | (11.1) |
| Pain in extremity | 2 | (7.4) | 1 | (3.7) | 3 | (5.6) |
| Contusion | | | 2 | (7.4) | 2 | (3.7) |
| Abscess oral | | | 1 | (3.7) | 1 | (1.9) |
| Bronchitis | 1 | (3.7) | | | 1 | (1.9) |
| Cellulitis | | | 1 | (3.7) | 1 | (1.9) |
| Chalazion | 1 | (3.7) | | | 1 | (1.9) |
| Clumsiness | | | 1 | (3.7) | 1 | (1.9) |
| Cognitive Disorder | | | 1 | (3.7) | 1 | (1.9) |
| Confusional state | | | 1 | (3.7) | 1 | (1.9) |
| Constipation | 1 | (3.7) | | | 1 | (1.9) |
| Diarrhoea | | | 1 | (3.7) | 1 | (1.9) |
| Dysgraphia | 1 | (3.7) | | | 1 | (1.9) |
| Epistaxis | 1 | (3.7) | | | 1 | (1.9) |
| Fall | | | 1 | (3.7) | 1 | (1.9) |
| Flatulence | 1 | (3.7) | | | 1 | (1.9) |
| Hepatic function abnormal | 1 | (3.7) | | | 1 | (1.9) |
| Increased tendency to bruise | 1 | (3.7) | | | 1 | (1.9) |
| Laryngitis | 1 | (3.7) | | | 1 | (1.9) |
| Mental impairment | | | 1 | (3.7) | 1 | (1.9) |
| Mouth ulceration | | | 1 | (3.7) | 1 | (1.9) |
| Muscle fatigue | | | 1 | (3.7) | 1 | (1.9) |
| Muscle spasms | 1 | (3.7) | | | 1 | (1.9) |
| Nasal congestion | | | 1 | (3.7) | 1 | (1.9) |
| Nasopharyngitis | 1 | (3.7) | | | 1 | (1.9) |
| Pruritus | 1 | (3.7) | | | 1 | (1.9) |
| Skin laceration | | | 1 | (3.7) | 1 | (1.9) |
| Skin lesion | 1 | (3.7) | | | 1 | (1.9) |
| Tympanic membrane perforation | 1 | (3.7) | | | 1 | (1.9) |
| Vision blurred | | | 1 | (3.7) | 1 | (1.9) |

Under one treatment, a subject with multiple occurrences of an adverse event is counted only once in the AE category. N=number of subject studied; n=number of subjects with at least 1 AE in the category. Only adverse events occurring at or after first drug intake are included.

Adverse Events Related to Study Drug and Most Frequent Events—n (%) of Subjects (all Patients in any Group) Safety Analysis Set

| Adverse Event | AQW051 15 mg | | | Placebo | | | Total | | |
|---|---|---|---|---|---|---|---|---|---|
| | AD N = 7 n (%) | MCI N = 20 n (%) | Total N = 27 n (%) | AD N = 9 n (%) | MCI N = 18 n (%) | Total N = 27 n (%) | AD N = 16 n (%) | MCI N = 38 n (%) | Total N = 54 n (%) |
| Patients with AE(s) | 1 (14.3) | 3 (15.0) | 4 (14.8) | 2 (22.2) | | 2 (7.4) | 3 (18.8) | 3 (7.9) | 6 (11.1) |
| Headache | | 2 (10.0) | 2 (7.4) | 2 (22.2) | | 2 (7.4) | 2 (12.5) | 2 (5.3) | 4 (7.4) |
| Clumsiness | | | | 1 (11.1) | | 1 (3.7) | 1 (6.3) | | 1 (1.9) |
| Cognitive disorder | | | | 1 (11.1) | | 1 (3.7) | 1 (6.3) | | 1 (1.9) |
| Confusional state | | | | 1 (11.1) | | 1 (3.7) | 1 (6.3) | | 1 (1.9) |
| Constipation | | 1 (5.0) | 1 (3.7) | | | | | 1 (2.6) | 1 (1.9) |
| Diarrhea | | | | 1 (11.1) | | 1 (3.7) | 1 (6.3) | | 1 (1.9) |
| Dysgraphia | | 1 (5.0) | 1 (3.7) | | | | | 1 (2.6) | 1 (1.9) |
| Flatulence | 1 (14.3) | | 1 (3.7) | | | | 1 (6.3) | | 1 (1.9) |
| Increased tendency to | | 1 (5.0) | 1 (3.7) | | | | | 1 (2.6) | 1 (1.9) |

-continued

| | AQW051 15 mg | | | Placebo | | | Total | | |
|---|---|---|---|---|---|---|---|---|---|
| Adverse Event | AD N = 7 n (%) | MCI N = 20 n (%) | Total N = 27 n (%) | AD N = 9 n (%) | MCI N = 18 n (%) | Total N = 27 n (%) | AD N = 16 n (%) | MCI N = 38 n (%) | Total N = 54 n (%) |
| Mental impairment | | | | 1 (11.1) | | 1 (3.7) | 1 (6.3) | | 1 (1.9) |
| Muscle spasms | | 1 (5.0) | 1 (3.7) | | | | | 1 (2.6) | 1 (1.9) |
| Pain in extremity | | 1 (5.0) | 1 (3.7) | | | | | 1 (2.6) | 1 (1.9) |
| Pruritus | | 1 (5.0) | 1 (3.7) | | | | | 1 (2.6) | 1 (1.9) |
| Vision blurred | | | | 1 (11.1) | | 1 (3.7) | 1 (6.3) | | 1 (1.9) |

Under one treatment, a subject with multiple occurrences of an adverse event is counted only once in the AE category. N=number of subject studied; n=number of subjects with at least 1 AE in the category. Only adverse events occurring at or after first drug intake are included.

What is claimed is:

1. A method for improving cognition in a human individual having findings consistent with a cognitive impairment, the method comprising:
    administering a therapeutically effective amount of 13.5 to 16.5 mg/day of (R)-3-(6-p-tolyl-pyridin-3-yloxy)-1-aza-bicyclo[2.2.2]octane- or a pharmaceutically acceptable salt thereof to the human individual, and
    achieving a statistically significant improvement in a cognitive function measurement obtained in the human individual, after the human individual is administered the (R)-3-(6-p-tolyl-pyridin-3-yloxy)-1-aza-bicyclo[2.2.2]octane,
    wherein the cognitive impairment is Mild Cognitive Impairment amnestic mild cognitive impairment.

2. A method of enhancing cognition in a human individual, the method comprising:
    administering a therapeutically effective amount 13.5 to 16.5 mg/day of (R)-3-(6-p-tolyl-pyridin-3-yloxy)-1-aza-bicyclo[2.2.2]octane or a pharmaceutically acceptable salt thereof to the human individual, and
    achieving a statistically significant improvement in a cognitive function measurement obtained in the human individual, after the human individual is administered (R)-3-(6-p-tolyl-pyridin-3-yloxy)-1-aza-bicyclo[2.2.2]octane,
    wherein the human individual has findings consistent with a cognitive impairment.

3. The method of claim 1, wherein the pharmaceutically acceptable salt thereof comprises a fumarate salt of (R)-3-(6-p-tolyl-pyridin-3-yloxy)-1-aza-bicyclo[2.2.2]octane.

4. The method of claim 3, wherein the pharmaceutically acceptable salt thereof comprises a mono-fumarate salt of (R)-3-(6-p-tolyl-pyridin-3-yloxy)-1-aza-bicyclo[2.2.2]octane.

5. The method of claim 1, wherein the therapeutically effective amount of (R)-3-(6-p-tolyl-pyridin-3-yloxy)-1-aza-bicyclo[2.2.2]octane or a pharmaceutically acceptable salt thereof is in the form of one or more capsules.

6. The method of claim 5, wherein each of the one or more capsules contains a unit dose of 4.5 to 5.5-mg of (R)-3-(6-p-tolyl-pyridin-3-yloxy)-1-aza-bicyclo[2.2.2]octane or a pharmaceutically acceptable salt thereof.

7. The method of claim 1, wherein the therapeutically effective amount of (R)-3-(6-p-tolyl-pyridin-3-yloxy)-1-aza-bicyclo[2.2.2]octane or a pharmaceutically acceptable salt thereof is administered after a meal.

8. The method of claim 2, wherein the pharmaceutically acceptable salt thereof comprises a fumarate salt of (R)-3-(6-p-tolyl-pyridin-3-yloxy)-1-aza-bicyclo[2.2.2]octane.

9. The method of claim 8, wherein the pharmaceutically acceptable salt thereof comprises a mono-fumarate salt of (R)-3-(6-p-tolyl-pyridin-3-yloxy)-1-aza-bicyclo[2.2.2]octane.

10. The method of claim 2, wherein the therapeutically effective amount of (R)-3-(6-p-tolyl-pyridin-3-yloxy)-1-aza-bicyclo[2.2.2]octane or the pharmaceutically acceptable salt thereof is in the form of one or more capsules.

11. The method of claim 10, wherein each of the one or more capsules contains a unit dose of 4.5 to 5.5 mg of (R)-3-(6-p-tolyl-pyridin-3-yloxy)-1-aza-bicyclo[2.2.2]octane or the pharmaceutically acceptable salt thereof.

12. The method of claim 2, wherein the therapeutically effective amount of (R)-3-(6-p-tolyl-pyridin-3-yloxy)-1-aza-bicyclo[2.2.2]octane or the pharmaceutically acceptable salt thereof is administered after a meal.

* * * * *

UNITED STATES PATENT AND TRADEMARK OFFICE
CERTIFICATE OF CORRECTION

PATENT NO. : 11,433,057 B2
APPLICATION NO. : 16/097750
DATED : September 6, 2022
INVENTOR(S) : Mihael H. Polymeropoulos It is certified that error appears in the above-identified patent and that said Letters Patent is hereby corrected as shown below:

In the Specification

Column 10, Line 24, the passage reading "butylmethylether (118.4 g) at temperature of about 50" is replaced with "butylmethylether (118.4 g) at temperature of about 50° C."

Signed and Sealed this
Twentieth Day of August, 2024

Katherine Kelly Vidal
*Director of the United States Patent and Trademark Office*